United States Patent [19]

Oosedo et al.

[11] Patent Number: 5,917,009
[45] Date of Patent: Jun. 29, 1999

[54] ALIPHATIC POLYAMINE AND METHOD OF PRODUCING THE SAME

[75] Inventors: Hiroki Oosedo; Ikuo Aoki; Shinji Kouchi, all of Ehime, Japan

[73] Assignee: Toray Industries, Inc., Japan

[21] Appl. No.: 08/996,436

[22] Filed: Dec. 22, 1997

[30] Foreign Application Priority Data

Jun. 20, 1997 [JP] Japan .................................. 9-164379

[51] Int. Cl.⁶ .................................................. C09J 163/00
[52] U.S. Cl. ........................ 528/480; 528/483; 528/501; 523/414; 523/420; 524/906
[58] Field of Search ............................ 524/906; 523/414, 523/420; 528/480, 483, 501

[56] References Cited

U.S. PATENT DOCUMENTS 4,609,692  9/1986  Huybrechts et al. .................... 523/439

*Primary Examiner*—Nathan M. Nutter
*Attorney, Agent, or Firm*—Austin R. Miller

[57] ABSTRACT

A liquid aliphatic polyamine material, sealed in a container, has an ammonia concentration of at most about 100 ppm, and can be made by removing volatile odor forming components from a liquid comprised of aliphatic polyamine, and enclosing it in an air-tight container, with substantially no oxygen present, whereby the odor of the liquid aliphatic polyamine is reduced to a very low level even after extended storage.

12 Claims, No Drawings

ALIPHATIC POLYAMINE AND METHOD OF PRODUCING THE SAME

BACKGROUND OF THE INVENTION

1. Field of the Invention

The present invention relates to an aliphatic polyamine material and a method of producing the same. More particularly, the invention relates to an aliphatic polyamine material for use as a curing agent for an epoxy resin in an epoxy resin composition, particularly, two-pack epoxy resin compositions, which are used as an adhesive, a coating material a molding materials matrix resin of composite material and the like, and also relates-to a method of producing the aliphatic polyamine material.

2. Description of the Related Art

Conventional two-pack epoxy resin compositions, wherein an epoxy resin and a curing agent are mixed immediately before use, are widely used as adhesives, coating material, primer, sealant, molding material, matrix resin of fiber-reinforced composite material, and the like. There are various advantages of two-pack epoxy resin compositions, such as being curable at ambient temperature, being usable without any solvent, absence of gas production during curing, excellent properties after being cured, and the like.

Aliphatic polyamines having excellent curability at normal temperatures are widely used as the main component of the curing agent of two-pack epoxy resin compositions.

However, many aliphatic polyamines have strong ammoniacal odors, which often cause problems in indoor use.

If a conventional two-type epoxy resin composition is used as an adhesive, or a coating material, a primer, a sealant, a matrix resin of a fiber-reinforced composite material, or the like in reform or repair of an interior of an already existing building, it is necessary to perform the work when people are not in the building, for example, during night hours or holidays, or to request people to stay away from the building during the reform or repair, considering the effect of the strong odor. Therefore, the strong foul odor of aliphatic polyamine often extends the time required for reforming or repairing.

SUMMARY OF THE INVENTION

Accordingly, it is an object of the present invention to reduce the odor of a liquid aliphatic polyamine to a very low level and, more particularly, to reduce the odor of a liquid comprised of an aliphatic polyamine for use as a curing agent, to a very low level.

An effective material to achieve those objects is an aliphatic polyamine material including a sealed-in liquid comprising an aliphatic polyamine. The liquid has a characteristic such that when the liquid is air-tightly bound with a gas and kept at 20° C., the ammonia concentration in equilibrium with the gas is at most about 100 ppm.

The method of producing aliphatic polyamine material of the present invention removes dissolved volatile odor components from liquid aliphatic polyamine, and then stores the liquid in an air-tight container with substantially no oxygen present.

DETAILED DESCRIPTION OF THE INVENTION

We have made the following discoveries regarding aliphatic polyamines:

(A) The problematic odor is not caused by the aliphatic polyamine itself but by highly volatile impurities such as ammonia. Removal of these impurities eliminates the odor.

(B) Even if such volatile odor components are removed before storage, storage in the presence of oxygen allows gradual production of volatile odor components and, therefore, production of foul odor. Storage substantially in the absence of oxygen does not permit production of foul odor.

According to the invention, the liquid comprised of aliphatic polyamine may be formed from a single aliphatic polyamine alone, or from a composition comprised of different kinds of aliphatic polyamines, or a composition containing one or more kinds of aliphatic polyamine as a main component and further containing other components.

If the liquid material is comprised of a single aliphatic polyamine, only removal of the volatile odorous components such-as ammonia from the aliphatic polyamine, is necessary, if oxygen is also removed by the process of removing volatile odor components.

If the liquid comprised of aliphatic polyamine according to the invention is formed from a mixture of a plurality of materials, either of two methods may be employed: one in which after volatile odor components are removed from each material, the materials are mixed in an atmosphere containing substantially no oxygen; or, in the alternative, a method in which after the materials are mixed, volatile odor components are removed from the mixture.

One example of a process for removing volatile odor components is vacuum degasification in which a liquid to be processed is subjected to reduced pressure in a sealed container for a predetermined length of time, and then brought back to atmospheric pressure, by introducing a gas that contains substantially no oxygen. The temperature for the pressure reducing process may be ambient temperature or an appropriately elevated temperature. Further, the liquid may be stirred or not, during the pressure reducing process.

In vacuum degasification, a gas containing substantially no oxygen may be passed through the liquid comprised of aliphatic polyamine. This method is effective to improve the efficiency in removing volatile odor components. The method advantageously reduces the processing time, particularly if a large amount of liquid is to be treated. Furthermore, a high-degree vacuum is not required in the pressure reducing process.

Another example is an aeration process using a gas containing substantially no oxygen. A gas containing substantially no oxygen is passed through the liquid at atmospheric pressure for a predetermined length of time. The temperature for the aeration process may be ambient temperature or an appropriately elevated temperature. Further, the liquid may be stirred or not, during the pressure reducing process.

Distillation may alternatively be used. In one method, distillation is performed in an atmosphere containing substantially no oxygen. In another method distillation is performed at a reduced pressure, and the liquid is brought back to atmospheric pressure using by introducing a gas containing substantially no oxygen. However, application of the distillation method may not be easy in the case of a liquid mixture wherein the boiling points of the components are considerably different.

A liquid comprised of aliphatic polyamine prepared by a method as described above is sealed into an air-tight container, with substantially no oxygen contained therein. An aliphatic polyamine material is thereby produced. Therefore, in the aliphatic polyamine material of the invention, a liquid comprised of an aliphatic polyamine is sealed in an air-tight container.

In a method of sealing a liquid in an air-tight container with substantially no oxygen contained therein, a liquid containing an aliphatic polyamine is placed or injected, together with a gas containing substantially no oxygen, into an air-tight container, and then sealed therein.

In another method that may be used, the capacity of an air-tight container is filled with a liquid comprised of aliphatic polyamine so that there is no space for gas.

In the invention, any air-tight container may be used as long as it has good sealing characteristics and low oxygen permeability. Examples include jars, bottles, cans, tanks, or ampoules formed of a metal, glass, plastics or the like. A squeeze-type tube or bag, or an extruding container comprised of a piston and a cylinder, may be preferred since such a container allows a desired amount of the liquid to be used without substantially causing the content of the container to be exposed to the external air.

The atmosphere containing substantially no oxygen, which is used in the processes described above, is preferably a gas in which the oxygen concentration is at most about 1 vol. %. More specifically, commercially available nitrogen or argon may preferably be used.

The aliphatic polyamine according to the invention is a compound having, in its molecule, a plurality of amino groups which connect carbons having $sp^3$ hybrid orbitals. If these conditions are satisfied, an amine having an aromatic ring in its molecule may be regarded as an aliphatic polyamine having an aromatic substitute. That is, such an amine having an aromatic ring is included in the scope of aliphatic polyamines according to the invention.

Examples of the aliphatic polyamine used in the aliphatic polyamine material according to the invention include: hexamethylenediamine, 2,5-dimethyl-2,5-hexanediamine, 2,2,4-trimethylhexamethylenediamine, diethylenetriamine, triethylenetriamine, tetraethylenepentamine, pentaethylenehexamine, 4-aminomethylocta-methylenediamine, 3,3'-iminobis(propylamine), 3,3'-methyliminobis(propylamine), bis(3-aminopropyl)ether, 1,2-bis(3-aminopropyloxy)ethane, menthanediamine isophoronediamine, bisaminomethylnorbornane, bis(4-aminocyclohexyl)methane, bis(4-amino-3-methylcyclohexyl)methane, 1,3-diaminocyclohexane, 3,9-bis(3-aminopropyl)-2,4,8,10-tetraoxaspiro[5,5]-undecane. Examples of aliphatic polyamines having an aromatic substitute group include m-xylylene diamine, tetrachloro-p-xylylene diamine, and the like.

Polyamideamines obtained through reactions between polymerized fatty acids (polyfunctional fatty acid mixture containing dimers of unsaturated fatty acids such as linolic acid) and polyamines, such as ethylenediamine, diethylenetriamine, triethylenetetramine, tetraethylenepentamine, pentaethylenehexmine, and the like may suitably be used.

Furthermore, compounds obtained by introducing aminoalkyl groups into the two terminals of a polyether, such as polyethylene glycol, polypropylene glycol and the like, and compounds obtained by introducing aminoalkyl groups into the two terminals of silicone compounds, such as polydimethylsiloxane, polymethylphenylsiloxane and the like, may also be suitably used.

According to the invention, the liquid comprised of aliphatic polyamine may also contain amines other than aliphatic polyamine, for example, imidazoles, or curing agents other than amines, for example, polymercaptans, which are dissolved or dispersed therein.

According to the invention, the liquid comprised of aliphatic polyamine may further contain a dissolved or dispersed phenol compound as a curing accelerator for the aliphatic polyamine. Preferable examples of the phenol compounds include diisopropylphenol, nonylphenol and the like.

According to the invention, the liquid comprised of aliphatic polyamine may further contain plasticizers, dyes, organic or inorganic particles such as organic pigments, carbon black, silica and the like, high molecular compounds, antioxidants, ultraviolet absorbents, coupling agents, surfactants, and the like which are dissolved or dispersed therein.

To evaluate the low-odor characteristic of the liquid comprised of aliphatic polyamine according to the invention, the ammonia concentration in a gas that is in equilibrium with the liquid comprised of aliphatic polyamine is measured, since ammonia is the greatest contributor to the odor of the liquid. The ammonia concentration in the gas indicates the upper limit of odor that can occur during operation using the liquid comprised of aliphatic polyamine. Under Henry's law, the ammonia concentration in the gas is proportional to the ammonia concentration in the liquid.

The ammonia concentration according to the invention refers to the ammonia concentration in a gas which is in equilibrium with the liquid aliphatic polyamine. The ammonia concentration according to the invention is measured by the following method:

A sealed container in which air and liquid aliphatic polyamine are contained is kept at 20° C. for 4 hours, attaining equilibrium. An end of an ammonia detector tube is inserted into the container through a small opening that does not disturb the ammonia concentration therein, the gas is drawn and any color change of the detector tube is read.

A commercially available ammonia detector tube may be used. Since there are several types of ammonia detector tubes with different detectable concentration ranges, a type suitable to the specimen must be used.

Examples of commercially available ammonia detector tubes include products by Gastec Kabushiki Kaisha. Gastec provides various types of ammonia detector tubes with different ammonia detectable concentration ranges as follows, from which a suitable type can be selected.

Ammonia No. 3L: 0.5–60 ppm

Ammonia No. 3La: 2.5–200 ppm

Ammonia No. 3M: 10–1000 ppm

Ammonia No. 3HM: 0.05–3.52%

Ammonia No. 3H: 0.2.–32%

If the ammonia concentration in the gas in equilibrium with the liquid comprised of aliphatic polyamine is 100 ppm or less, irritation will not become problem although there may be slight ammoniacal odor. Therefore, an ammonia concentration of about 100 ppm is acceptable but an ammonia concentration of about 10 ppm is more preferable since there is no substantial ammoniacal odor.

According to the invention, if the liquid comprised of aliphatic polyamine is used as a curing agent of an epoxy resin, the seal package of the aliphatic polyamine material produced according to the invention is opened only immediately before it is used. The content is mixed with the epoxy resin to form an epoxy resin composition, which is then promptly used. In the aliphatic polyamine material produced according to the invention, the liquid comprised of aliphatic polyamine is made substantially free from volatile odor components and sealed in an air-tight container with substantially no oxygen present. Therefore, no odor is produced by oxidation of the aliphatic polyamine, even after a long period of storage; no odor will be released when the container is opened.

The expression "epoxy resin" refers to an epoxy compound having a plurality of epoxy groups in the molecule.

Examples of the epoxy resin to be used in the practice of the invention include bisphenol A-type epoxy resin, bisphenol F-type epoxy resin, bisphenol S-type epoxy resin, biphenyltype epoxy resin, naphthalene-type epoxy resin, novolactype epoxy resin, epoxy resin having a fluorene skeleton, epoxy resin derived from copolymer of a phenol compound and dicyclopentadiene, glycidyl ether-type epoxy resin such as diglycidylresorcinol, tetrakis(glycidyloxyphenyl)ethane, tris(glycidyloxyphenyl)methane, and the like, glycidylamine-type epoxy resins such as tetraglycidyl-diaminodiphenylmethane, triglycidylaminophenol, triglycidylaminocresol, tetraglycidylxylenediamine and the like, alicyclic epoxy resins such as vinylcyclohexenediepoxide and the like, and mixtures of any of these compounds.

It is also possible to compound into the epoxy resin composition a compound having one epoxy group in its molecule as a reactive diluent. Examples of compounds having one epoxy group in its molecule include phenyl glycidyl ether, butyl glycidyl ether, allyl glycidyl ether, styrene oxide, octylene oxide and the like.

It is also possible to compound into the epoxy rein composition a compound, other than epoxy compounds, which reacts with amines. Examples of components that react with amines include isocyanates such as hexamethylene diisocyanate, tolylene diisocyanate and the like, and further, $\alpha,\beta$-unsaturated carbonyl compounds that undergo Michael addition reactions with amines.

The epoxy resin composition may further contain other components, for example, plasticizers, dyes, organic or inorganic particles such as organic pigments, carbon black, silica, alumina, clay minerals and the like, macromolecular compounds, antioxidants, ultraviolet absorbents, coupling agents, surfactants, and the like.

Components having adsorption capacity, such as silica, alumina, clay minerals, may preferably be included since such component will adsorb any small amounts of volatile odor-forming components that might remain even after using the volatile odor component removing process.

The epoxy resin composition may be used as an adhesive, a coating materials primer, a sealant, a molding material, a matrix resin of a fiber-reinforced composite material, or the like.

To use the epoxy resin composition as a matrix resin of a fiber-reinforced composite material, a hand lay-up method may be employed wherein a sheet-formed reinforcing fiber is impregnated with an epoxy resin composition, and the sheets are laminated and then cured either at room temperature or higher. Examples of reinforcing fibers to be used include carbon fiber, glass fiber, aramid fiber and the like. The fibers may be formed into a sheet-like form, such as a woven fabric, a mat, a unidirectional sheet, or the like.

The hand lay-up method is used in production of component parts of a bath tub, a tank, a hull, a motor vehicle, and for repair or reinforcement of various fiber-reinforced composite materials, concrete structures and the like.

Examples of the method for using the epoxy resin composition as a matrix resin of a fiber-reinforced composite material further include filament winding a resin transfer molding and the like.

In the aliphatic polyamine material produced according to the invention, the liquid comprised of aliphatic polyamine is made substantially free from volatile odor components and sealed in an air-tight container with substantially no oxygen contained. Therefore, no odor will be produced by oxidation of aliphatic polyamine even during or after a long period of storage, so that no odor will be released when the container is opened. Therefore, if it is used as a curing agent in an epoxy rein composition that is used as an adhesive, a coating material, a primer, a sealant, a matrix of a fiber-reinforced composite material for repair or reinforcement, in an indoor operation, more particularly, in reform or repair of an interior of a building which is in use, the aliphatic polyamine material of the invention does not produce any irritating odor or annoyance to people who use the building and, therefore, can suitably be used in such a situation.

The invention will be further described in detail with reference to Examples.

EXAMPLE 1

Two specimens were prepared in each of which 50 g of commercially obtained bis(aminomethyl)norbornane (by Mitsui Toatsu Fine Chemicals, Inc.) was placed in a flask having a capacity of about 200 cm$^3$ and equipped with a three-way cock. A strong ammonia odor was emitted by the specimens. The ammonia concentration detected by an ammonia detector tube (Ammonia No. 3HM by Gastec) was 1400 ppm.

One of the two specimens was subjected to degasification for 10 minutes under a reduced pressure of about 200 Pa using a vacuum pump. After the degasification, no ammonia odor was noticeable from the specimen. The ammonia concentration detected by an ammonia detector tube (Ammonia No. 3L by Gastec) was 2 ppm.

The other specimen was also subjected to degasification for 10 minutes under a reduced pressure of about 200 Pa using a vacuum pump. Subsequently, nitrogen gas was introduced into the container to return to atmospheric pressure. After a three-way cock was airtightly closed, the specimen was left in an oven at 50° C. for 20 hours. The container was then cooled to 20° C. for detection of ammonia concentration. The ammonia concentration detected was 4 ppm.

EXAMPLE 2

50 g of bis(aminomethyl)norbornane (by Mitsui Toatsu Fine Chemicals, Inc.) the same as used in Example 1 was placed in a flask having a capacity of about 200 cm$^3$. Nitrogen gas was passed through the liquid at a flow rate of 100 cm$^3$/minute for an hour using a glass tube whose end was placed in the liquid. After the treatment, no ammonia odor as before the treatment was noticeable. The ammonia concentration in the container was detected as 8 ppm. 30 cm$^3$ of the treated bis(aminomethyl)norbornane was collected by a syringe, and injected into a flask having a capacity of about 100 cm$^3$ and equipped with a three-way cock, whose interior atmosphere had been replaced with nitrogen gas. After the cock was air-tightly closed, the specimen was left in an oven at 50° C. for 20 hours. The specimen was cooled to 20° C. for detection of ammonia concentration. The ammonia concentration detected was 2 ppm.

EXAMPLE 3

Bis(aminomethyl)norbornane was degasified as in Example 1 and brought back to atmospheric pressure using nitrogen gas. Under a nitrogen gas stream a specimen of 10 cm$^3$ was measured into a glass syringe. After air inside the syringe was discharged by pushing the piston while holding and directing the syringe upward, the tip end of the syringe was sealed by a rubber cap. The specimen was left in an oven at 50° C. for 20 hours. After the specimen was cooled to 20° C., the cap was removed and the specimen was placed into another container to check the odor. No ammonia odor was noticeable. The ammonia concentration detected was 2 ppm.

COMPARATIVE EXAMPLE 1

Bis(aminomethyl)norbornane was degasified as in Example 1 and brought back to atmospheric pressure using air. After the three-way cock was closed to airtightly seal the container, the container was left in an oven at 50° C. for 20 hours. After the container was cooled to 20° C., the three-way cock was opened to check the odor. Strong ammonia odor was apparent and noticeable. The ammonia concentration detected by an ammonia detector tube (Ammonia No. HM by Gastec) was 2000 ppm.

EXAMPLE 4

25 g of bis(aminomethyl)norbornane (by Mitsui Toatsu Fine Chemicals, Inc.), 25 g of isophoronediamine (Wako Pure Chemical Industries, Ltd.) and 2 g of Aerosil 380 (Nippon Aerosil Co., Ltd.) were placed in flask having a capacity of about 200 cm$^3$ and equipped with a three-way cock. After the mixture was stirred for 20 minutes by a magnetic stirrer, the mixture was degasified at a reduced pressure of about 200 Pa for 10 minutes using a vacuum pump. The degasified specimen was brought back to atmospheric pressure using nitrogen gas. After the three-way cock was closed to air-tightly seal the container, the container was left in an oven at 50° C. for 20 hours. After the container was cooled to 20° C., the cock was opened to check the odor. No ammonia odor was noticeable. The ammonia concentration detected was 5 ppm.

EXAMPLE 5

1 kg of bis(aminomethyl)norbornane (by Mitsui Toatsu Fine Chemicals, Inc.) was placed into a cylindrical separable flask equipped with a gas introducing tube and a stirring blade. While nitrogen gas was gradually introduced into bis(aminomethyl)norbornane through the gas introducing tube and the liquid was stirred, the pressure was reduced to about 400 Pa for 2 hours using an aspirator. No ammonia odor was noticeable from the treated liquid. The ammonia concentration detected was 5 ppm.

450 cm$^3$ Of the treated bis(aminomethyl)norbornane was poured into a metallic can having a capacity of about 500 cm$^3$ with nitrogen gas blown into the can. After the can was immediately sealed with an air-tight lid the specimen was left in an oven at 50° C. for 20 hours. After the container was cooled to 20° C., the ammonia concentration detected was 8 ppm. No ammonia odor was smelled.

EXAMPLE 6

Two specimens were prepared in each of which 50 g of commercially obtained triethylenetetramine (by ACI Japan Ltd.) was placed in a flask having a capacity of about 200 cm$^3$ and equipped with a three-way cock. Strong ammonia odor was apparent from the specimens. The ammonia concentration detected was 2500 ppm.

One of the two specimens was subjected to degasification for 10 minutes under a reduced pressure of about 200 Pa using a vacuum pump. After the degasification, no ammonia odor as before the degasification was noticeable from the specimen. The ammonia concentration detected was 40 ppm.

The other specimen was also subjected to degasification for 10 minutes under a reduced pressure of about 200 Pa using a vacuum pump. Subsequently, nitrogen gas was introduced into the container to return to atmospheric pressure. After the three-way cock was airtightly closed, the specimen was left in an oven at 50° C. for 20 hours. The container was then cooled to 20° C. for detection of ammonia concentration. The ammonia concentration detected was 70 ppm.

EXAMPLE 7

Two specimens were prepared in each of which 50 g of commercially obtained diethylenetriamine (by ACI Japan Ltd.) and 40 g of bis(4-amino-3-methylcyclohexyl)methane (by ACI Japan Ltd.) were placed in a flask having a capacity of about 200 cm$^3$ and equipped with a three-way cock. A strong ammonia odor was noticed from the specimens. The ammonia concentration detected was 1000 ppm.

One of the two specimens was subjected to degasification for 10 minutes under a reduced pressure of about 200 Pa using a vacuum pump. After the degasification, no ammonia odor as before the degasification was noticed from the specimen. The ammonia concentration detected was 16 ppm.

The other specimen was also subjected to degasification for 10 minutes under a reduced pressure of about 200 Pa using a vacuum pump. Subsequently, nitrogen gas was introduced into the container to return to atmospheric pressure. After the three-way cock was airtightly closed, the specimen was left in an oven at 50° C. for 20 hours. The container was then cooled to 20° C. for detection of ammonia concentration. The ammonia concentration detected was 20 ppm.

EXAMPLE 8

50 g of m-xylylene diamine (by Mitsubishi Gas Chemical Company Inc.) was weighed in a flask having a capacity of about 200 cm$^3$. Strong ammonia odor was noticeable from the specimen. The ammonia concentration detected was 500 ppm.

Subsequently, the specimen was subjected to distillation under reduced pressure while nitrogen is being passed through. A distillation fraction of a boiling point of 80–95° C./1 mmHg was obtained. No ammonia odor was noticeable from this liquid. The ammonia concentration detected was 60 ppm.

Further, 30 cm$^3$ of m-xylylene diamine after the distillation was taken into a syringe, and injected into a flask having a capacity of about 100 cm$^3$ and equipped with a three-way cock, whose interior atmosphere had been replaced with nitrogen gas. After the specimen was left in an oven at 50° C. for 20 hours, the specimen was cooled to. 20° C. for detection of ammonia concentration. The ammonia concentration detected was 80 ppm.

We claim:

1. A combination of a container and liquid aliphatic polyamine, wherein said liquid aliphatic polyamine is airtightly sealed in said container without a gas or with a gas containing substantially no oxygen, and when said liquid is air-tightly contained together with a gas containing substantially no oxygen and kept at 20° C., the ammonia concentration in said gas at equilibrium is at most about 100 ppm.

2. A method of producing an aliphatic polyamine comprising the steps of:

removing volatile odor components from a liquid aliphatic polyamine, and storing said liquid in an air-tight container, with substantially no oxygen present therein.

3. A method of producing an aliphatic polyamine according to claim 2, wherein said step of removing volatile odor components is performed by degasifying said liquid aliphatic polyamine under reduced pressure and then resuming atmospheric pressure by combining it with a gas that contains substantially no oxygen.

4. A method of producing an aliphatic polyamine according to claim 2, wherein the step of removing volatile odor components is performed by passing a gas that contains substantially no oxygen, through said liquid of aliphatic polyamine.

5. A method of producing an aliphatic polyamine according to claim 2, wherein the step of enclosing said liquid in an air-tight container, with substantially no oxygen contained therein, is performed by enclosing said liquid together with a gas that contains no oxygen in said air-tight container.

6. A method of producing an aliphatic polyamine according to claim 3, wherein the step of enclosing said liquid in an air-tight container, with substantially no oxygen contained therein, is performed by enclosing said liquid together with a gas that contains no oxygen in said air-tight container.

7. A method of producing an aliphatic polyamine according to claim 4, wherein the step of enclosing said liquid in an air-tight container, with substantially no oxygen contained therein, is performed by enclosing said liquid together with a gas that contains no oxygen in said air-tight container.

8. A method of producing an aliphatic polyamine according to claim 2, wherein the step of enclosing said liquid in said air-tight container, with substantially no oxygen contained therein, is performed by filling the entire capacity of said air-tight container with said liquid.

9. A method of producing an aliphatic polyamine according to claim 3, wherein the step of enclosing said liquid in said air-tight container, with substantially no oxygen contained therein, is performed by filling the entire capacity of said air-tight container with said liquid.

10. A method of producing an aliphatic polyamine according to claim 4, wherein the step of enclosing said liquid in said air-tight container, with substantially no oxygen contained therein, is performed by filling the entire capacity of said air-tight container with said liquid.

11. The combination according to claim 1, wherein said aliphatic polyamine is a curing agent of an epoxy resin.

12. The method according to claim 2, wherein said aliphatic polyamine is a curing agent of an epoxy resin.

* * * * *